United States Patent
Mikaelian (10) Patent No.: US 11,213,199 B2
(45) Date of Patent: Jan. 4, 2022

(54) SYSTEMS AND METHODS FOR FUNCTIONAL EVALUATION OF RETINA

(71) Applicant: NIDEK CO., LTD., Aichi (JP)

(72) Inventor: Gareguin Mikaelian, San Pedro, CA (US)

(73) Assignee: NIDEK CO., LTD., Aichi (JP)

( * ) Notice: Subject to any disclaimer, the term of this patent is extended or adjusted under 35 U.S.C. 154(b) by 492 days.

(21) Appl. No.: 16/336,189

(22) PCT Filed: Jun. 14, 2018

(86) PCT No.: PCT/IB2018/000698
§ 371 (c)(1),
(2) Date: Mar. 25, 2019

(87) PCT Pub. No.: WO2018/229541
PCT Pub. Date: Dec. 20, 2018

(65) Prior Publication Data
US 2019/0223711 A1    Jul. 25, 2019

Related U.S. Application Data

(60) Provisional application No. 62/519,539, filed on Jun. 14, 2017.

(51) Int. Cl.
*A61B 3/08* (2006.01)
*A61B 3/00* (2006.01)
*A61B 3/12* (2006.01)
*A61B 3/024* (2006.01)
*A61B 3/06* (2006.01)
*A61B 3/032* (2006.01)

(52) U.S. Cl.
CPC .............. *A61B 3/08* (2013.01); *A61B 3/0008* (2013.01); *A61B 3/0041* (2013.01); *A61B 3/024* (2013.01); *A61B 3/032* (2013.01); *A61B 3/066* (2013.01); *A61B 3/12* (2013.01)

(58) Field of Classification Search
CPC ....... A61B 3/08; A61B 3/0008; A61B 3/0041; A61B 3/042; A61B 3/032; A61B 3/066; A61B 3/12; A61B 3/10; A61B 3/14
USPC ................ 351/201, 206, 246, 205, 200, 221
See application file for complete search history.

(56) References Cited

U.S. PATENT DOCUMENTS 7,309,125 B2 *   12/2007   Pugach ................ A61B 3/0091
                                                                  351/201

* cited by examiner

*Primary Examiner* — Hung X Dang
(74) *Attorney, Agent, or Firm* — Rankin, Hill & Clark LLP (57) ABSTRACT

A method of analyzing the degree of abnormality in the eye is provided, and in the method at least some portion of the functional evaluation of the eye's visual function is performed by presenting visual stimuli in mesopic conditions. A visual function examination device is provided, and in the device the spectral composition of the stimuli is generated by a projection or display device, and the said projection or display device can be adjusted so that individual receptor types can be excited by the said stimuli.

5 Claims, 7 Drawing Sheets

SYSTEMS AND METHODS FOR FUNCTIONAL EVALUATION OF RETINA

CROSS-REFERENCE TO RELATED APPLICATIONS

This application claims the benefit of U.S. Provisional patent application, Ser. No. 62/519,539 entitled "SYSTEMS AND METHODS FOR FUNCTIONAL EVALUATION OF RETINA," filed on Jun. 14, 2017; the entirety of the above-noted application(s) is incorporated by reference herein.

TECHNICAL FIELD

The present disclosure relates to advanced diagnostics of ocular diseases using visual field and color testing.

BACKGROUND

Age related maculopathy (ARM) and its late stage—the age related macular degeneration (AMD) are the leading causes of blindness in people over 60. The pathomechanisms and progression of ARM are complex and involve an interplay between genetics, oxidative stress, metabolic stress, and a number of environmental risk factors. Therefore early detection of the disease is highly beneficial, since the patient can make lifestyle changes that may slow down the progression.

As demonstrated in a number of recent clinical studies in early AMD the sensitivity of rods decreases more rapidly than the sensitivity of cones. The rod dark adaptation recovery also slows down with AMD progression. There were a number of efforts to capitalize on these observations in order to develop an early biomarker for ARM. The goal of these approaches is to selectively measure the rod function without stimulating the cones. Since rods are mainly responsible for dark adapted vision and become saturated in photopic conditions, rod specific measurements are usually performed in scotopic condition.

The scotopic visual field examination can be performed using a scoptopic microperimeters such as NIDEK's MP-1S and MP-3S or a scotopic perimeter, such as the Medmont DAC Perimeter. Such instruments project very dim stimuli on an even dimmer (0.01 asb) background. Cones are not sensitive at such low light conditions, and just the rod function can be evaluated. Unfortunately, scotopic visual field examination requires the patient to undergo a prolonged dark adaptation prior to testing. This increases the preparation and chair time, and requires a dedicated dark room. Such complications significantly limit the adoption of scotopic perimetry and microperimetry in the clinic and mainly limit the use of such techniques to research and clinical trials.

Performing receptor type-specific evaluation or retinal function in brighter than scotopic conditions will simplify the exam procedure and may result in a wide adoption of such tests. This will benefit a large number of patients, since detection of early signs of ARM will allow them to start an early prevention and treatment regimen.

BRIEF DESCRIPTION

According to one aspect, a device for performing visual field examination of the subject and having a capability to separately evaluate different receptor types by controlling the spectral composition of background and stimuli.

In one aspect the visual filed testing is performed using a perimeter.

In another aspect of the disclosure the visual field testing is performed using a microperimeter device with a capability to image the fundus and use the image for tracking and accurate location of stimuli.

In some aspects, a four or more primary color projection or display system is used to project background or stimuli or both.

In other aspects a tunable light source is used to present stimuli or background or both.

The brightness and the spectral composition of the background and stimuli may be selected based on knowledge of anatomical or physiological parameters, normative data, individual patient measurements, or any combination of the above.

DETAILED DESCRIPTION

Problems to be Solved by the Invention

The present disclosure is directed towards systems and methods for performing accurate evaluation of the eye, including receptor-specific testing in brighter than scotopic conditions. Regarding an evaluation of an eye in general, the disclosures of WO2016/145367, U.S. Patent Application Publication No. 2018/0070814, and U.S. Pat. No. 8,931,904 are hereby incorporated by reference.

Rod sensitivity is compromised in many retinal pathologies like pigmentary retinopathy, rod-cone dystrophy, retinal telangiectasia, congenital night blindness, and central serous chorioretinitis. Recent histological evidence, moreover, shows that rods can be damaged earlier than cones in the early stages of advanced macular degeneration, particularly at the parafoveal level, where they are found in greater numbers. In line with this morphological data, there is evidence that affected subjects prematurely present difficulty in adapting to twilight vision.

Traditionally, rod-specific functional evaluation of the retina is performed using scotopic perimeters and microperimeters, such as the Medmont's dark adapted chromatic (DAC) perimeter or NIDEK's MP-1S and MP-3S scotopic microperimeters.

Scotopic perimetry and microperimetry is performed in extremely dark conditions. This requires a dedicated dark room, and limits the possibility of the operator to assist with the examination. Moreover, a lengthy dark adaptation is needed—the patient needs to be in a complete darkness for up to 40 minutes prior to the examination start. Considering such logistical difficulties, it is clear why this useful technique is not used in clinics for early diagnostics of retinal diseases.

To promote the adoption of rod specific testing and provide new means of early retinal disease diagnosis, it may be advantageous to perform a functional evaluation of the retina in mesopic conditions. Mesopic adaptation time is significantly shorter than scotopic adaptation and can be performed using dark glasses while the patient is in the waiting room. Thus, a visual field measuring device, that is capable of selectively stimulating rods and testing rod function in mesopic conditions may be very advantageous for early disease detection.

During mesopic examination, rods are not saturated and they respond to brightness changes. However, testing of rod function in mesopic conditions is complicated because cones can also be excited and conventional visual field examination performed in mesopic conditions usually evaluates the function of rods and cones simultaneously. This reduces the amount of useful signal and complicates the interpretation of the examination results.

Means of Solving the Problems

Figure 1:
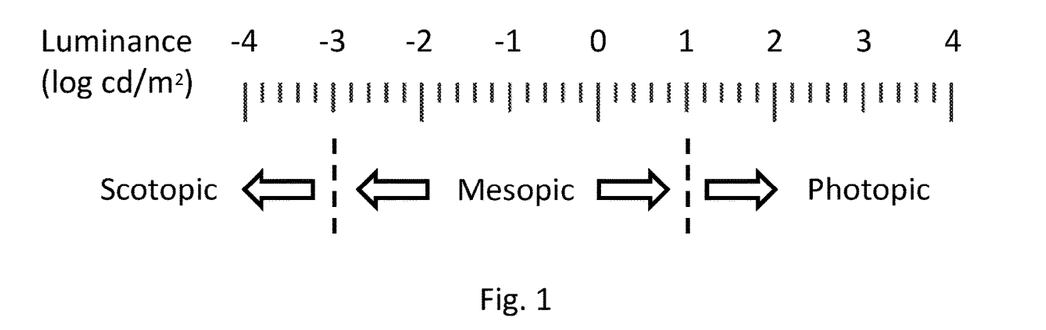
FIG. 1 is an illustration of visual function dependence on luminance level.

FIG. 1 illustrates the dependence of the visual function on the luminance levels. The scotopic region lies between $10^{-6}$ cd/m$^2$ and $10^{-3}$ cd/m$^2$. This luminance range is below the cone threshold and scotopic vision is exclusively rod based. At luminances above about 10 cd/m$^2$ rods start to saturate and above 100 cd/m$^2$ they are completely saturated. This is the photopic region where the vision is dominated by cones. Between $10^{-3}$ cd/m$^2$ and 10 cd/m$^2$ both rods and cones contribute to vision. This is the mesopic region.

Figure 2:
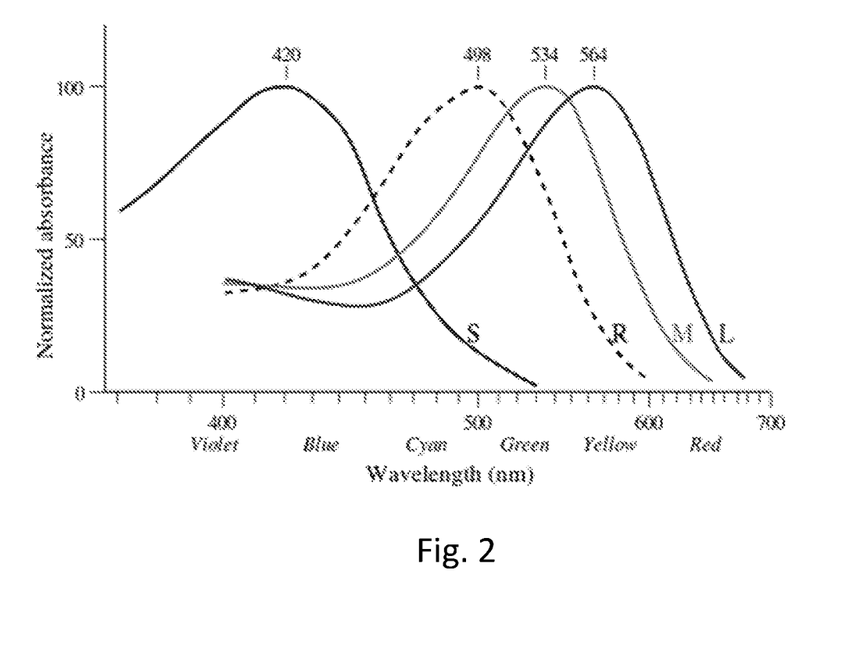
FIG. 2 is an illustration of spectral sensitivities of rods (R), and L-, M-, and S-cones.

The mesopic visual function is further complicated by the fact that each three cone types and rods have specific spectral sensitivities. FIG. 2 illustrates the spectral sensitivities of rods, and L-, M-, S-cones. Due to significant overlaps between said sensitivity functions different cone types and rods cannot be individually examined using a single color stimuli. However, using multi-color stimuli or stimuli with a well controlled spectral composition it is possible to isolate individual cone types and rods for selective examination.

According to one or more aspects, advanced diagnostics of ocular diseases may be provided by utilizing a perimeter or microperimeter capable of generating stimuli with accurately controlled spectral composition.

Isolation of individual cone types can be performed in color testing application using three primary color projection system. In some aspects isolation of rods and individual cone excitations can be done by using a four or more primary color projection system. In such aspect it may be advantageous to use a four-color projection system where the spectral distribution of all four colors is linearly independent. In such case the spectral distribution of the projected color can be described as a 1×4 matrix $a=[p_1, p_2, p_3, p_4]$, where $p_n$ represents the intensity of the n-th source in the projection system. Given the spectral distribution of the projected light $Q(\lambda)$ it is possible to calculate individual receptor excitation intensities:

$$L = C\int Q(\lambda)l(\lambda) \qquad \text{Eq. 1}$$

$$M = C\int Q(\lambda)m(\lambda) \qquad \text{Eq. 2}$$

$$S = C\int Q(\lambda)s(\lambda) \qquad \text{Eq. 3}$$

$$R = C\int Q(\lambda)r(\lambda) \qquad \text{Eq. 4}$$

Here L,M,S,R represent three cone types and rods respectively, l,m,s,r are the receptor sensitivity functions as illustrated in FIG. 2, and C is a constant related to the pupil size.

Since $Q(\lambda)$ is a linear combination of spectral distributions of four individual sources it is possible to rewrite Eqs. 1-4 as:

$$E = aA, \qquad \text{Eq. 5}$$

where A is the 4×4 transformation matrix defined by:

$$A = C \begin{pmatrix} \int P_1(\lambda)l(\lambda) & \int P_1(\lambda)m(\lambda) & \int P_1(\lambda)s(\lambda) & \int P_1(\lambda)r(\lambda) \\ \int P_2(\lambda)l(\lambda) & \int P_2(\lambda)m(\lambda) & \int P_2(\lambda)s(\lambda) & \int P_2(\lambda)r(\lambda) \\ \int P_3(\lambda)l(\lambda) & \int P_3(\lambda)m(\lambda) & \int P_3(\lambda)s(\lambda) & \int P_3(\lambda)r(\lambda) \\ \int P_4(\lambda)l(\lambda) & \int P_4(\lambda)m(\lambda) & \int P_4(\lambda)s(\lambda) & \int P_4(\lambda)r(\lambda) \end{pmatrix} \qquad \text{Eq. 6}$$

For a given excitation vector $E=[l,m,s,r]$ the solution to the Eq. 5 will provide the four-color matrix necessary to achieve this excitation.

In one aspect, in order to isolate rod excitation while silencing cones it is advantageous to select the intensities of four primary colors such that $a=[p_1, p_2, p_3, p_4]$ is the solution of the $$\begin{pmatrix} 0 \\ 0 \\ 0 \\ 1 \end{pmatrix} = C[p_1, p_2, p_3, p_4] \qquad \text{Eq. 7}$$

$$\begin{pmatrix} \int P_1(\lambda)l(\lambda) & \int P_1(\lambda)m(\lambda) & \int P_1(\lambda)s(\lambda) & \int P_1(\lambda)r(\lambda) \\ \int P_2(\lambda)l(\lambda) & \int P_2(\lambda)m(\lambda) & \int P_2(\lambda)s(\lambda) & \int P_2(\lambda)r(\lambda) \\ \int P_3(\lambda)l(\lambda) & \int P_3(\lambda)m(\lambda) & \int P_3(\lambda)s(\lambda) & \int P_3(\lambda)r(\lambda) \\ \int P_4(\lambda)l(\lambda) & \int P_4(\lambda)m(\lambda) & \int P_4(\lambda)s(\lambda) & \int P_4(\lambda)r(\lambda) \end{pmatrix}$$

In some aspects of the invention the matrix coefficients in Eqs. 6 and 7 may be calculated based on population based normative database. In other aspects of the invention, the said matrix coefficients may be evaluated specifically for individual patients. In such aspect, the said coefficients may be selected based on a vision examination performed by a different instrument, or they may be selected in the course of the examination performed by the same instrument.

In some aspects of the invention the spatial distribution of the rods and cones may be taken into account and coefficients in the said transformation matrix A may be dependent on the location on the retina.

In some aspects it may be advantageous to isolate various cone types, or simultaneously isolate and excite a subset of four receptor types while silencing the others.

In other aspects of the invention all receptors may be excited with individually controlled excitations.

Yet in another aspect of the invention, it may be advantageous to perform the visual testing in photopic conditions where the rods are completely saturated.

Yet in another aspect of the invention, it may be possible to conduct the visual examination in scotopic conditions where cones are fully silenced.

In some aspects of the invention it may be advantageous to further expand the number of primary colors to achieve better isolation and silencing of individual receptors.

In other aspects of the disclosure it may be advantageous to use a light source with tunable wavelength or spectral composition source.

EXAMPLE EMBODIMENTS

Figure 3:
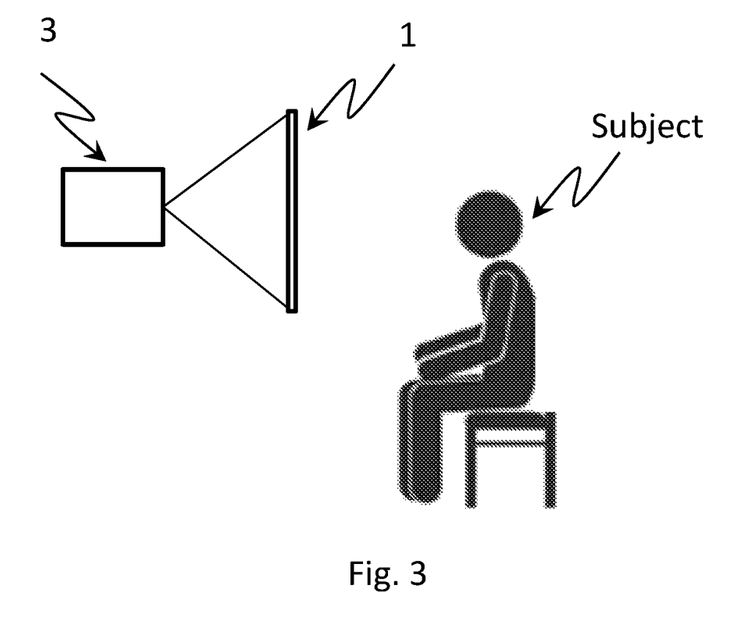
FIG. 3 is an illustration of an exemplary configuration of the device comprising a screen and a projector.

In one embodiment of the invention the patient's head may be positioned in front of a screen 1 and a background and stimuli may be projected onto the screen 1, as illustrated in FIG. 3. The screen 1 may be flat or curved to accommodate a large field of view. In the said configuration, a four or more primary color projector system 3 may be configured to project background and stimuli onto the said screen 1. An eye tracking device may be used to verify and track the patient's fixation during the examination.

In this embodiment the projection device can be a digital micromirror device, liquid crystal based projector, laser projector, or any other projection system capable of delivering four or more primary colors. In another aspect of invention the projection system may be capable of delivering light with a well controlled spectral composition. One example of such embodiment may include a DLP optical grating device capable of spectral shaping of the continuous light source. To a person skilled in the art it is apparent that other types of tunable light sources may be used to generate light with a controlled spectral composition.

Figure 4:
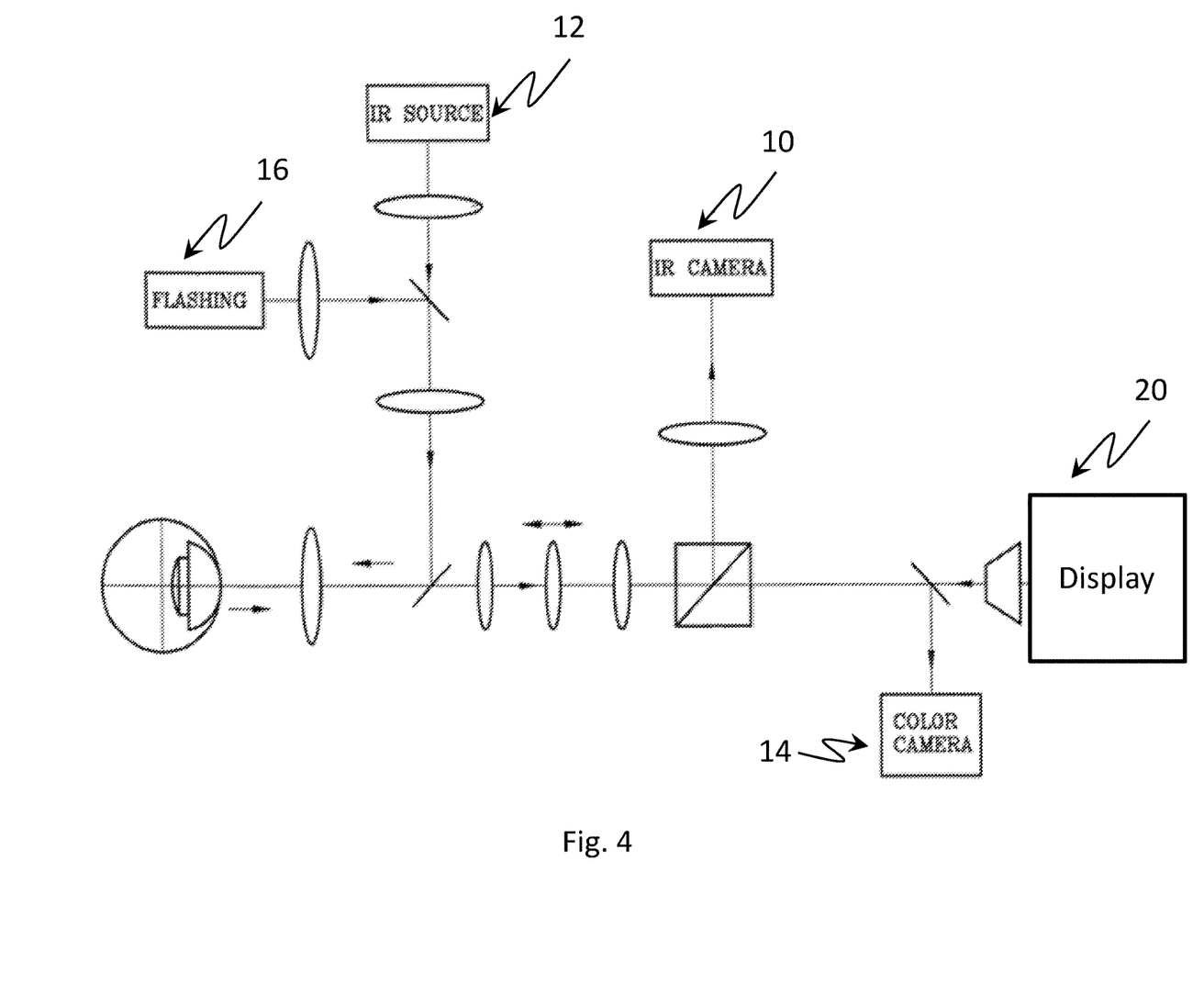
FIG. 4 is an illustration of an exemplary configuration of a visual field testing device with fundus observation capability.

In another embodiment, the examination may be performed using a microperimetry device, where the patient's fundus image is obtained during examination and the stimuli are presented at known locations on the retina. FIG. 4 illustrates the schematic diagram of such device. The devices comprises an IR camera 10 and IR source 12 for fundus observation and a color camera 14 and flashing source 16 for fundus imaging and a display or projector system 20 for presenting visual stimuli. The said display or projector system may be a liquid crystal device, DMD device, or another type of color or display projection system. A combination of several systems and several types of display or projection systems may be used to achieve the spectral composition desirable for selective stimulation or rods or various types of cones.

In some embodiments the device may be table mounted, hand-held or head-mounted. Some embodiments may be able to test single eye at a time, while other embodiments may allow testing both eyes of the patient sequentially or simultaneously.

Additional embodiments may comprise gaze fixation target and anterior segment observation camera. An infrared anterior segment observation camera may be used to monitor fixation, perform eye-tracking, or allow the operator to monitor the patient during the examination.

Exemplary Embodiments of a Multi-Color Stimulation System

Multi-color visual stimulation systems may be implemented using projection technology, display technology, or a combination of the two.

Figure 5:
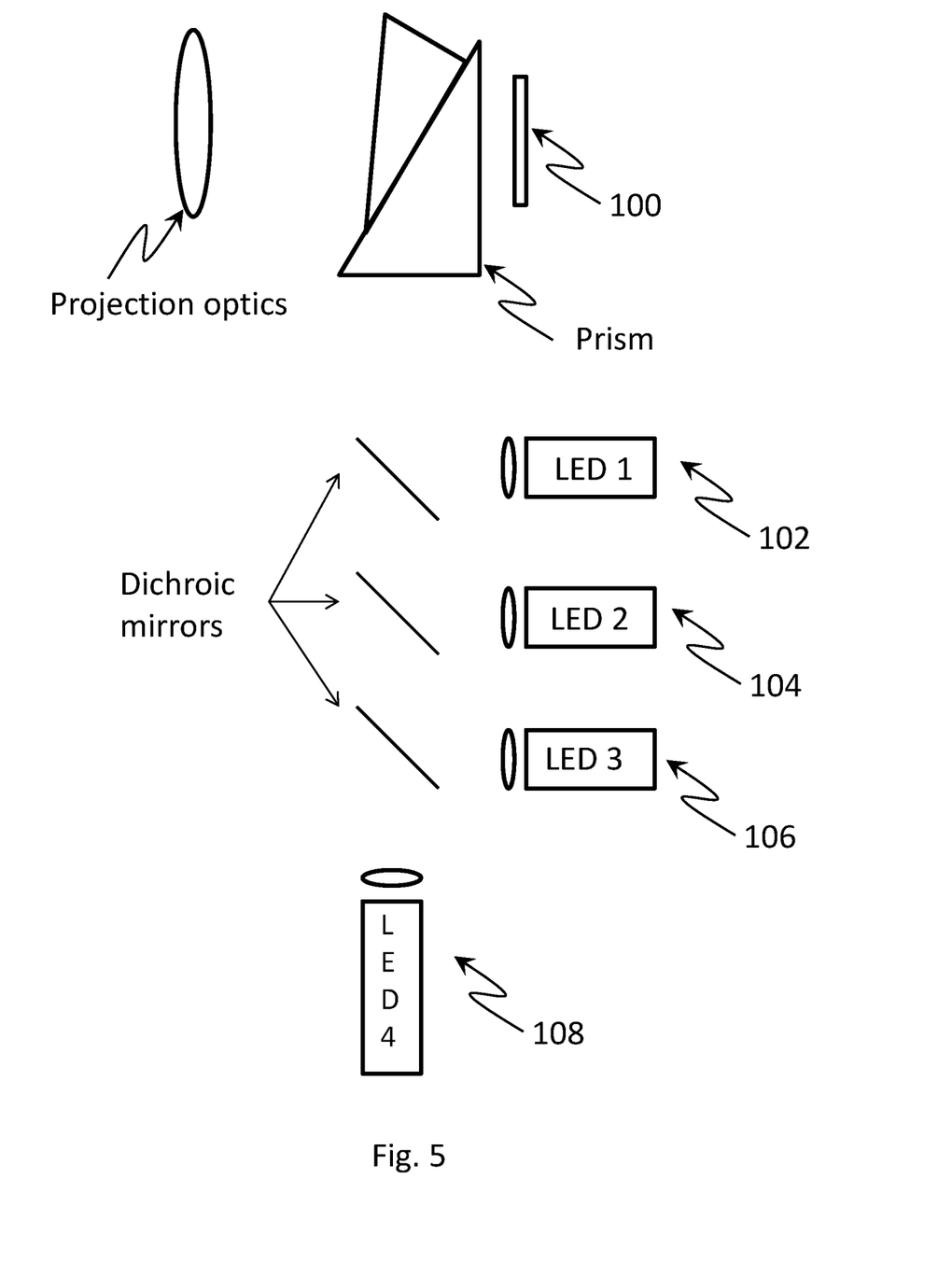
FIG. 5 is an illustration of an exemplary schematic diagram of a light engine using a 4-primary color DLP projector.

In one embodiment the stimuli may be presented using a DLP device. In general, a DLP projector comprises a DMD chip 100, which is illuminated by a light source. The light source can be a combination of color LEDs, or a broadband source with a filter wheel with a rotation that is synchronized to the operation of the micromirrors on the DMD chip. Most conventional LED based DLP projectors use three LEDs 102, 104, 106 for red, green, and blue color. The light from these LEDs is combined using a series of optical filters, dichroic mirrors, and beam splitters. FIG. 5 depicts an exemplary schematic diagram of a light engine of a 4-primary color DLP projector (e.g. an fourth LED 108). In this system it is possible to extend the number of primary colors by adding more LED light sources, filters, dichroic mirrors, and beam splitters.

In another embodiment, a filter wheel based DLP projector may be utilized with a number of sections in the filter wheel that is required for producing stimuli with needed spectral composition.

In another embodiment, a four or more color LCD projector may be used to project stimuli.

Yet in another embodiment, two projectors each with less than four primary colors but with different spectral composition may be aligned so that they can present a stimulus at the same location on the visual field. In such embodiment the projectors may be DLP projectors, LCD projectors, or projectors utilizing another technology.

The projection system to present the stimuli may be a front projection system, rear projection system, or a combination of the two.

Figure 6:
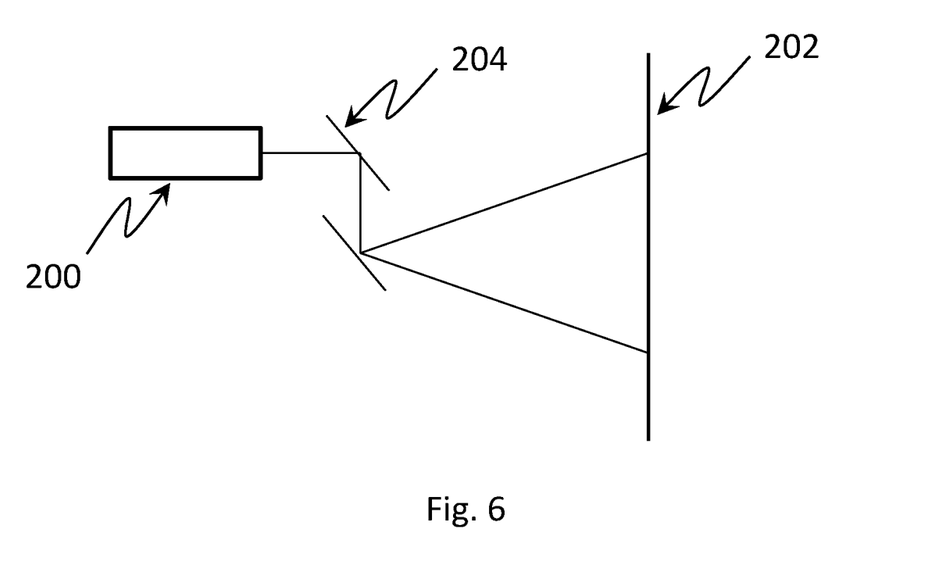
FIG. 6 is an illustration of an exemplary schematic diagram of a scanning projection system with a tunable light source.

In another embodiment depicted in FIG. 6 a tunable light source 200 may be used to project the background and stimuli. This system consists of a screen 202, tunable focused light source 200, and a scanning system 204 capable of changing the direction of the focused beam coming out of the light source. The said system may be used as a stand-alone projection system, or may be used in combination with a projection or LCD screen.

In another embodiment the stimuli may be presented on a multicolor display, such as a LCD, LED, plasma, CRT or other color display technology.

Yet in another embodiment the background may be presented on a multicolor display, and the stimuli may be projected onto the said display using a projection system.

Yet in another embodiment, a combination of a display screen with a projection system may be used but, the background may be generated by the projector, while the stimulus is generated by the display screen.

In most conventional perimeters, the stimuli are added on top of the background, meaning that for a given spectral composition of the background and stimulus, there are no wavelength ranges, wherein the intensity of the background at a given wavelength is brighter than the intensity of the stimulus.

In one embodiment, it may be advantageous to modulate the intensity and spectral composition of the stimulus such that at a certain wavelength, or combination of wavelengths the intensity of the stimulus is less than the intensity of the background.

Exemplary Strategies for Testing of a Visual Function.

In some embodiments, a normative data from a number of subjects may be used to evaluate the rod function.

In another embodiment, changes in rod sensitivity and dark adaptation may be used to evaluate a progression or onset of a retinal disease. Such changes may be evaluated during follow-up examination. In one embodiment, the evaluation can be performed by recording a reaction of the subject to be tested.

Figure 7:
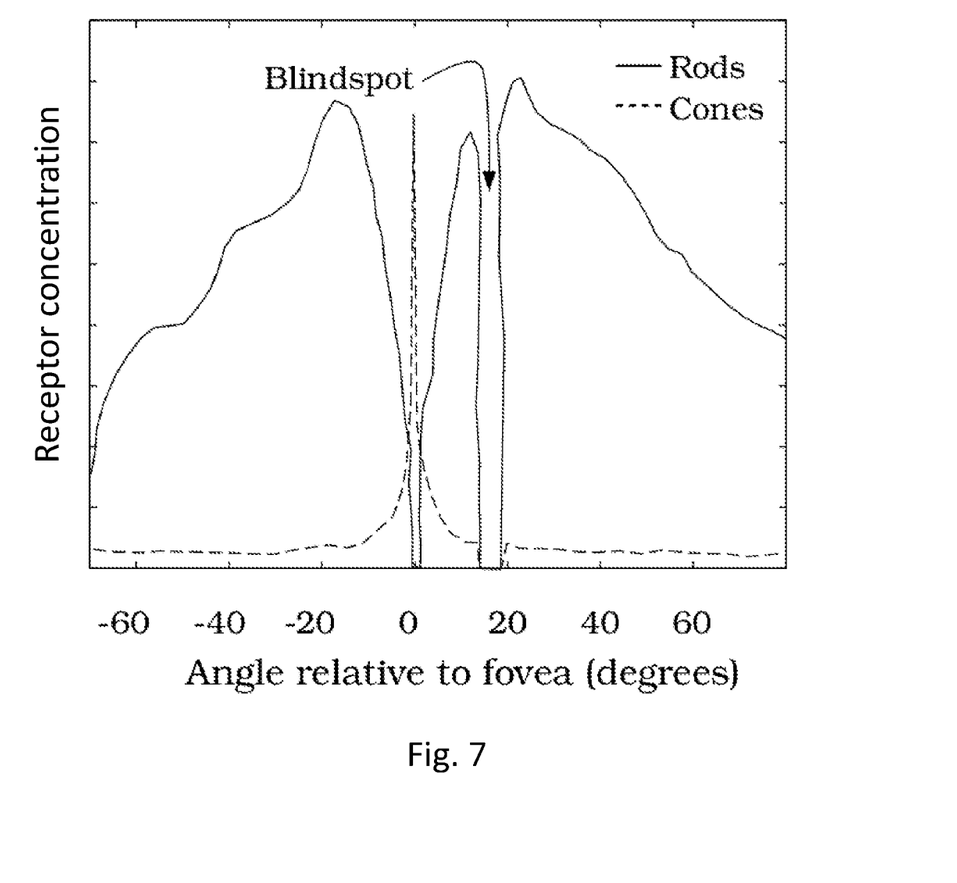
FIG. 7 is an illustration of rod and cone density in the retina.

In all embodiments it may be beneficial to perform the visual examination at different locations of the retina. The rod concentration as a function of eccentricity is shown in FIG. 7. From this illustration, it is apparent that rods are absent in the fovea and their density peaks at the parafoveal region at about 10-degrees. Therefore, by comparing the visual function at the central and parafoveal regions, it may be possible to characterize the rod function.

In one implementation of such examination it may be possible to select a stimulus that is not visible in the foveal region, due to the lack of contrast in cones. The spectral composition of the stimulus may be adjusted to an individual based on determining the responses to one or more stimuli. Once the stimulus is adjusted so it cannot be seen by the cones, it may be presented in the parafoveal region to test the rod function.

Yet in another implementation the adjustment of the spectral composition of the stimulus may be performed in photopic conditions. In such conditions rods are completely saturated and do not contribute to vision. Once a suitable spectral composition of the stimulus is determined a rod-isolating examination may be performed in mesopic conditions using the said suitable spectral composition.

In another implementation not only the spectral composition of the stimulus, but also the spectral composition of the background may be adjusted based on the subject's specific anatomy and physiology.

Definitions

AMD—age-related macular degeneration
ARM—age related maculopathy
CRT—cathode ray tube
DAC—dark adapted chromatic
DLP—digital light processing
DMD—digital micromirror device
LCD—liquid crystal display
LED—light emitting diode

The invention claimed is:

1. A method of analyzing a degree of abnormality in an eye of a subject to be tested, comprising: presenting visual stimuli in mesopic conditions to perform a functional evaluation of a visual function of the eye; and recording a reaction of the subject wherein a spectral composition of the presented visual stimuli is selected so that only one receptor type of the eye is excited, wherein a normative database is used to predict the sensitivity of remaining receptor types of the subject to be tested.

2. A method of claim 1, wherein the spectral composition of the presented visual stimuli is selected so that only rods are excited, wherein a normative database is used to predict a cone sensitivity of the subject to be tested and the spectral composition of the presented visual stimuli for rod testing is determined based on the predicted cone sensitivity.

3. A method of analyzing a degree of abnormality in an eye of a subject to be tested, comprising: presenting visual stimuli in mesopic conditions to perform a functional evaluation of a visual function of the eye; and recording a reaction of the subject wherein a spectral composition of the presented visual stimuli is selected so that only one receptor type of the eye is excited, wherein the visual stimuli presented in the mesopic conditions are for testing specific receptor type function in the first region of a retina of the eye where said receptors are present, and the method further comprises: presenting stimuli in the second region of the retina of the eye to measure the sensitivity or relative density of remaining types of the receptors of the eye; and determining the spectral composition of the presented visual stimuli for testing receptor function based on the measured sensitivity in the second region.

4. A method of claim 3, wherein the visual stimuli presented in the mesopic conditions are for testing rod function in parafoveal and other regions of a retina of the eye where rods are present, and the method further comprises: presenting stimuli in a foveal region of the retina to measure a cone sensitivity or relative cone density of the eye; and determining the spectral composition of the presented visual stimuli for testing rod function based on the measured cone sensitivity in the foveal region.

5. A method of analyzing a degree of abnormality in an eye of a subject to be tested, comprising: presenting visual stimuli in mesopic conditions to perform a functional evaluation of a visual function of the eye; and recording a reaction of the subject wherein a spectral composition of the presented visual stimuli is selected so that only one receptor type of the eye is excited, wherein a cone sensitivity or relative cone density of the subject to be tested is evaluated in photopic conditions, and the spectral composition of the presented visual stimuli for testing rod function is determined based on the evaluated cone sensitivity.

* * * * *